US010383975B2

(12) United States Patent
Sambusseti

(10) Patent No.: US 10,383,975 B2
(45) Date of Patent: Aug. 20, 2019

(54) ABSORBABLE DEVICE FOR BONE REGENERATION

(71) Applicant: Antonio Sambusseti, Cremona (IT)

(72) Inventor: Antonio Sambusseti, Cremona (IT)

( * ) Notice: Subject to any disclaimer, the term of this patent is extended or adjusted under 35 U.S.C. 154(b) by 41 days.

(21) Appl. No.: 15/515,878

(22) PCT Filed: Sep. 29, 2015

(86) PCT No.: PCT/IB2015/057438
§ 371 (c)(1),
(2) Date: Mar. 30, 2017

(87) PCT Pub. No.: WO2016/059494
PCT Pub. Date: Apr. 21, 2016

(65) Prior Publication Data
US 2017/0304490 A1    Oct. 26, 2017

(30) Foreign Application Priority Data

Oct. 14, 2014  (IT) .............................. MI2014A1786

(51) Int. Cl.
*A61L 27/22*   (2006.01)
*A61F 2/28*    (2006.01)
*A61L 27/32*   (2006.01)
*C08L 67/04*   (2006.01)

(52) U.S. Cl.
CPC ............. *A61L 27/227* (2013.01); *A61L 27/32* (2013.01); *A61L 2430/02* (2013.01); *C08L 67/04* (2013.01)

(58) Field of Classification Search
CPC ................ A61F 2/28; A61F 2002/2835; A61F 2002/30062; A61L 27/58; A61L 2430/02; A61L 2430/24
See application file for complete search history.

(56) References Cited

U.S. PATENT DOCUMENTS

| 4,987,665 A | 1/1991 | Dumican et al. |
| 2006/0084930 A1 | 4/2006 | Dhanaraj et al. |
| 2009/0157087 A1* | 6/2009 | Wei .................... A61B 17/7097 606/99 |
| 2010/0203155 A1* | 8/2010 | Wei ....................... A61F 2/4603 424/549 |

FOREIGN PATENT DOCUMENTS

GB    2259252 A    3/1993

OTHER PUBLICATIONS

Gupta et al., Polyester and Polyamides, Chapter 15—Polyester and nylon based textiles in biomedical engineering, 2008, Woodhead Publishing Series in Textiles, pp. 441-504.*
Liu et al., Polymeric Scaffolds for Bone Tissue Engineering, Annals of Biomedical Engineering, vol. 32, No. 3, Mar. 2004, pp. 477-486.*

(Continued)

*Primary Examiner* — Brian A Dukert
(74) *Attorney, Agent, or Firm* — Vorys, Sater, Seymour and Pease LLP

(57) ABSTRACT

A device for bone regeneration includes a fill element adapted to be inserted, during use, in a cavity present in a bone of a patient; the fill element being made of PGA fibers.

19 Claims, 2 Drawing Sheets

(56) References Cited

OTHER PUBLICATIONS

International Search Report and Written Opinion dated Nov. 27, 2015 for PCT/IB2015/057438 to Antonio Sambusseti filed Sep. 29, 2015.
Webster's Third New International Dictionary of the English Language Unabridged, Interstitial, p. 1183, Merriam-Webster Inc., Springfield, MA, U.S.A.
Know Your Knits, Threads, Threads magazine, Nov. 19, 2008.
Wikipedia, Warp knitting, URL: <https://en.wikipedia.org/wiki/Warp_knitting>, retrieved from the Internet Dec. 5, 2018.
McGraw-Hill Dictionary of Scientific and Technical Terms Fifth Edition, Interstitial, McGraw-Hill, Inc., 1994, ISBN 0-07-113584-7.

* cited by examiner

ABSORBABLE DEVICE FOR BONE REGENERATION

CROSS-REFERENCE TO RELATED APPLICATIONS

This is a § 371 National Stage Application of International Application No. PCT/IB2015/057438 filed on Sep. 29, 2015, claiming the priority of Italian Patent Application No. MI2014A001786 filed on Oct. 14, 2014.

FIELD OF THE INVENTION

The object of the present invention is a bone regeneration device.

The application of the present invention lies in the cases in which it is necessary to integrate the bone tissue of a patient following a bone fracture, for example.

Indeed, after the reassembly of a bone fraction, there may be a gap in the fitting of the fracture edges that must be filled.

BACKGROUND OF THE INVENTION

According to the prior art, such cavities are filled with so-called bone substitutes. The following bone substitutes are used: hydroxyapatite and/or tricalcium sulfate, minerals containing calcium, in powder, paste or microgranule form or in another form.

The bone substitutes—inserted in the bone cavities to be filled—solidify, thus creating a hard substance which, by filling the cavity, restores the integrity of the bone.

Nevertheless, even when solidified, these materials cannot ensure the same mechanical characteristics as the natural bone tissue.

Consequently, even in the reassembled and healed bone, the portion made of bone substitute has lower hardness than the rest of the bone tissue and represents a weakening zone for the entire bone.

Some known technical solution, such as the one disclosed in US2006/0084930, make use of absorbable material defined by a multilayered fabric which could also be usable for repairing bone lost due to disease or injury; according to said solution, prior the disposing of the tissue, a site for implantation has to be prepared so as to dispose inside it the tissue.

Other solution, as disclosed in GB2259252, make use of a biomedical material defined by a flexible fiber-meshed micro tube suitable for being inserted into the space defined by the defect of the bone; said tube is disclosed as having a well-defined diameter comprised in a specific range in order not to make difficult the insertion of the tube into the bone defect.

Other known solution making use of absorbable material is disclosed in U.S. Pat. No. 4,987,665 which describes a tubular article which can be used for bone or ligament repair and which, for the implantation, requires the forming of a passage on the bones through which said tubular article is inserted.

As can be noticed also said solutions, although disclosing the use of absorbable material, they all require a specific and precise realization of a site for the insertion of the material.

There are two basic types of knit fabrics—weft knits and warp knits—and it's the direction in which the yarns making up the fabric are looped that determines which type of knit the fabric is.

FIG. 2 Shows a Weft knit. A weft knit is made with a single yarn looped horizontally to from a row, or course, with each row building on the previous one. A hand-knitted fabric is a weft knit.

FIG. 3 shows a Warp knit. A wrap knit is made with numerous parallel yarns that are looped vertically at the same time.

SUMMARY OF THE INVENTION

In this context, the technical task at the base of the present invention is to propose a bone regeneration device which overcomes the drawback of the abovementioned prior art.

In particular, object of the present invention is to provide a bone regeneration device that allows a complete physiological, functional and mechanical restoration for a patient's bone.

The specified technical task and the specified object are substantially achieved by a bone regeneration device comprising the technical characteristics set forth in one or more of the enclosed claims.

BRIEF DESCRIPTION OF THE DRAWINGS

Further characteristics and advantages of the present invention will be clearer from the exemplifying and therefore non-limiting description of a preferred but not exclusive embodiment of a bone regeneration device, as illustrated in the enclosed drawings, in which.

Figure 1:
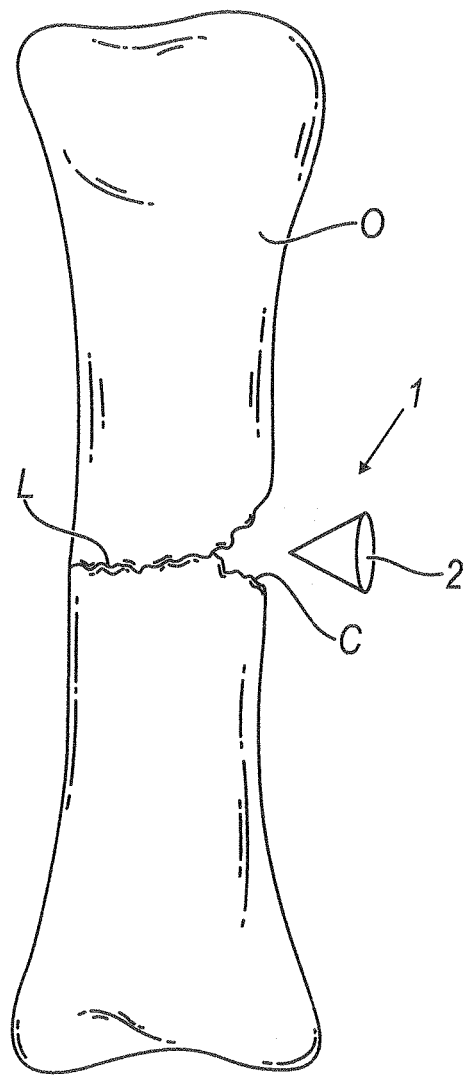
FIG. 1 is a schematic view of the bone regeneration device in accordance with the present invention.
Figure 2:
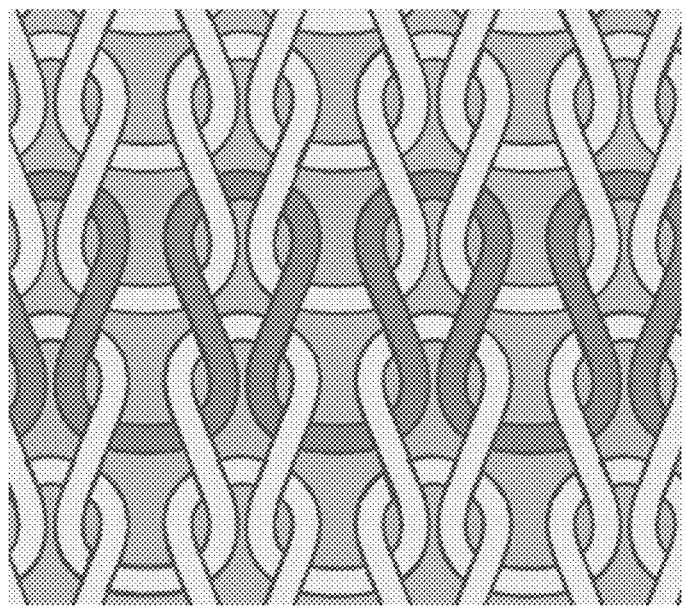
FIG. 2 shows a conventional Weft knit.
Figure 3:
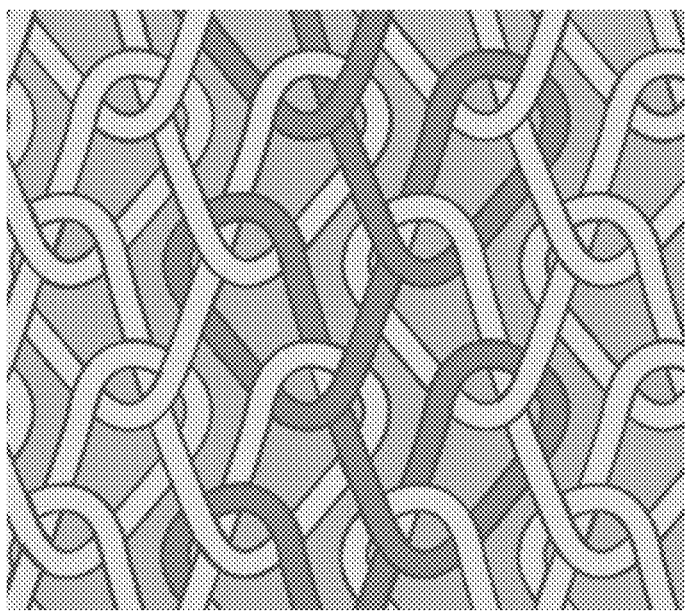
FIG. 3 shows a conventional Warp knit.

With reference to the enclosed drawing, reference number overall indicates a bone regeneration device in accordance with the present invention.

DETAILED DESCRIPTION OF THE PREFERRED EMBODIMENTS

The device 1 comprises a fill element 2 which, during use, is inserted in a cavity "C" present on a bone "O" of a patient.

In particular, the cavity "C" can be situated at a reassembled fracture line "L" of the bone "O" itself.

The fill element 2 is made of a solid resorbable material.

More precisely, the fill element 2 is made of PGA fibers (polyglycolide or polyglycolic acid), preferably homopolymer. PGA is a highly biocompatible and resorbable polymer.

The average resorption time of the PGA fibers is approximately one month.

Advantageously, during the resorption of the fill element 2, there is the formation of bone tissue, which progressively takes the place of the dissolving PGA fibers.

The bone tissue being formed simultaneously with the dissolution of the fill element 2 completely fills the cavity "C" and has the same nature as the bone tissue of the patient's bone.

Consequently, the newly-formed bone tissue possesses the same mechanical characteristics as the original bone tissue.

In such a manner, the cavity is filled with naturally compatible tissue and does not alter the mechanical and physiological characteristics of the repaired bone.

Advantageously, the fill element 2 is made of PGA fiber fabric.

In such a manner, once the fill element 2 is inserted in the cavity "C", the fabric is impregnated with blood and in particular with plasma, which facilitates the bone regeneration.

The fabric can be obtained by weaving the PGA thread in various ways, giving rise to a knitted fabric, a woven fabric or a non-woven fabric.

Preferably, the fabric is a knitted fabric, still more preferably a warp knitted fabric.

In such cases, the fabric has a rougher surface capable of assuming a net configuration with sufficiently small meshes.

In detail, its weft is such that its interstitial space is less than 200 μm, preferably around 160 μm, corresponding to an average area of the holes equal to approximately 0.02 mm$^2$.

Furthermore, the fabric is preferably textured so as to give it even greater surface roughness and greater rigidity.

In a first embodiment, the fill element 2 can be shaped in a manner such that it is substantially counter-shaped with respect to the shape of the cavity to be filled. The fabric with which the fill element 2 is obtained is sufficiently flexible to allow the operator to bend it, so as to counter-shape the fill element 2 at the time of implant.

In a second embodiment, the fill element 2 is already shaped. In particular, the fill element 2 is already counter-shaped with respect to the cavity "C" to be filled.

In particular, the fill element 2 can have a cylindrical, parallelepiped, pyramid or cone shape, or it can have another shape.

For the obtainment of the fill elements 2, three-dimensional weaving techniques can also be used that allow the obtainment non-hollow solids made of PGA fiber.

In particular, such techniques provide for the weaving and subsequent superimposition of fabric layers of suitable shapes, which are then connected to each other by means of suture points made of the same material as the fabric, i.e. in this case PGA.

During obtainment, fill elements 2 can be created of any shape and size that are completely solid, i.e. without any cavity therein.

The use of the PGA fiber allows obtaining solids provided with a softness sufficient to be slightly compressed, in order to better adapt the fill element 2 to the shape and/or size of the cavity "C" to be filled.

In addition, the fill elements 2 can be easily cut, with scissors or scalpels, by the operator in the operating room in order to adapt the shape and/or size thereof to the cavity "C" to be filled.

The invention attains the preset object.

Indeed, due to the implant of the absorbable fill element made of PGA, there is a bone regeneration process that fills the bone cavity in which it is inserted.

As already stated, given that the regenerated bone tissue is equivalent to that of the bone on which the device is implanted, there is no lessening of the mechanical characteristics of the reassembled and healed bone.

The healing process is therefore more complete and does not leave any significant consequences.

The invention claimed is:

1. A device for bone regeneration comprising
    a fill element adapted to be inserted, during use, in a cavity present in a bone of a patient and to be impregnated, during use, with blood and plasma to facilitate bone regeneration; said fill element being made of PGA fibers,
    wherein said fill element consists of the PGA fibers;
    wherein the fill element has outside surface,
    wherein said fill element is non-hollow,
    wherein the PGA fibers extend continuously across the entire fill element within the outside surface,
    wherein said fill element is counter-shapeable or counter-shaped with respect to the bone cavity in which the fill element is insertable,
    wherein the PGA fibers of the fill element have a resorption time of approximately one month, wherein the fill element is made of PGA fiber fabric of the PGA fibers.

2. The device according to claim 1, wherein the fill element is made of superimposed layers of said PGA fabric which are connected to each other by suture points made of PGA.

3. The device according to claim 1, wherein the PGA fiber fabric is a knitted fabric.

4. The device according to claim 1, wherein the fill element is counter-shapeable with respect to the bone cavity in which the fill element is insertable.

5. The device according to claim 1, wherein the fill element is counter-shaped with respect to the bone cavity in which the fill element is insertable.

6. The device according to claim 5, wherein said fill element is cylinder-shaped, parallelepiped-shaped, pyramid-shaped or cone-shaped.

7. The device according to claim 3, wherein said fabric is a warp knitted fabric.

8. The device according to claim 3, wherein the fabric has a net configuration having a weft such that its interstitial spaces are, respectively, less than 200 μm, corresponding to an average area of holes equal to approximately 0.02 mm$^2$.

9. The device according to claim 3, wherein the fabric has a net configuration having a weft such that its interstitial spaces are, respectively, less than 160 μm, corresponding to an average area of holes equal to approximately 0.02 mm$^2$.

10. The device according to claim 1, wherein the fabric has a net configuration having a weft is such that its interstitial spaces are, respectively, less than 200 μm, corresponding to an average area of holes equal to approximately 0.02 mm$^2$.

11. The device according to claim 1, wherein the fabric has a net configuration having a weft such that its interstitial spaces are, respectively, less than 160 μm, corresponding to an average area of holes equal to approximately 0.02 mm$^2$.

12. The device according to claim 1, wherein the fill element is cylinder-shaped.

13. The device according to claim 1, wherein the fill element is parallelepiped-shaped.

14. The device according to claim 1, wherein the fill element is pyramid-shaped or cone-shaped.

15. The device according to claim 5, wherein the fill element is pyramid-shaped or cone-shaped.

16. The device according to claim 1, wherein the fill element is made of PGA fiber fabric of the PGA fibers, wherein the fabric is a knitted fabric.

17. The device according to claim 4, wherein the fill element is made of superimposed layers of said PGA fabric which are connected to each other by suture points made of PGA.

18. The device according to claim 5, wherein the fill element is made of superimposed layers of said PGA fabric which are connected to each other by suture points made of PGA.

19. The device according to claim 6, wherein said fill element is cylinder-shaped, parallelepiped-shaped, pyramid-shaped or cone-shaped, wherein the fill element is made of superimposed layers of said PGA fabric which are connected to each other by suture points made of PGA.

\* \* \* \* \*